United States Patent [19]
Leifeld et al.

[11] Patent Number: 5,974,629
[45] Date of Patent: Nov. 2, 1999

[54] METHOD AND APPARATUS FOR MEASURING FIBER LENGTH AND NEP NUMBER IN A CARDING MACHINE

[75] Inventors: Ferdinand Leifeld, Kempen; Stefan Schlichter, Viersen, both of Germany

[73] Assignee: Trützschler GmbH & Co. KG, Mönchengladbach, Germany

[21] Appl. No.: 08/988,421

[22] Filed: Dec. 10, 1997

[30] Foreign Application Priority Data

Dec. 13, 1996 [DE] Germany .......................... 196 51 893

[51] Int. Cl.$^6$ .................................................. D01G 15/00
[52] U.S. Cl. ................................... 19/98; 19/99; 19/102; 19/106 R; 19/108; 19/109; 19/297
[58] Field of Search .................. 19/98, 99, 102, 19/106 R, 108, 109, 297

[56] References Cited

U.S. PATENT DOCUMENTS

| | | | |
|---|---|---|---|
| 2,795,012 | 6/1957 | Gibson et al. ............................ | 19/98 |
| 4,434,531 | 3/1984 | Mondini ................................... | 19/99 |
| 4,953,265 | 9/1990 | Scheinhutte ............................ | 19/106 R |
| 5,181,295 | 1/1993 | Demuth et al. ......................... | 19/65 A |
| 5,361,450 | 11/1994 | Shofner et al. ......................... | 19/66 R |
| 5,398,380 | 3/1995 | Leifeld .................................... | 19/98 |
| 5,430,301 | 7/1995 | Shofner et al. ......................... | 250/461.1 |
| 5,624,924 | 4/1997 | Sauter et al. ........................... | 19/98 |
| 5,642,553 | 7/1997 | Leifeld .................................... | 19/98 |
| 5,692,267 | 12/1997 | Leifeld .................................... | 19/106 R |
| 5,822,972 | 10/1998 | Patelke et al. ......................... | 19/98 |

FOREIGN PATENT DOCUMENTS

| | | |
|---|---|---|
| 0 410 429 | 1/1991 | European Pat. Off. . |
| 0 485 881 | 5/1992 | European Pat. Off. . |
| 0 738 792 | 10/1996 | European Pat. Off. . |
| 32 18 114 A1 | 12/1982 | Germany . |
| 41 06 331 | 9/1991 | Germany . |
| 32 18 114 C2 | 10/1995 | Germany . |
| 627 498 | 1/1982 | Switzerland . |
| 2 300 004 | 10/1996 | United Kingdom . |

*Primary Examiner*—William Stryjewski
*Attorney, Agent, or Firm*—Venable; Gabor J. Kelemen

[57] ABSTRACT

A method of measuring fiber material while being processed by fiber processing components of a carding machine, includes the following steps: measuring fiber length and nep number at an outlet of the carding machine; applying measured values of the fiber length and nep number to a control and regulating device; forming, in the control and regulating device, optimized machine setting data for the fiber length and the nep number; and applying the optimized machine setting data to at least one of the fiber processing components affecting fiber length and nep number.

17 Claims, 4 Drawing Sheets

METHOD AND APPARATUS FOR
MEASURING FIBER LENGTH AND NEP
NUMBER IN A CARDING MACHINE

CROSS REFERENCE TO RELATED APPLICATION

This application claims the priority of German Application Ser. No. 196 51 893.8 filed Dec. 13, 1996, which is incorporated herein by reference.

BACKGROUND OF THE INVENTION

This invention relates to a method and an apparatus for its practice, integrated in a carding machine. The apparatus is of the known type in which the staple (fiber length) and nep number are measured at the output of the carding machine and regulation is effected based on the sensed signals.

In a known process as disclosed in published European patent application Ser. No. 0 410 429, at the output of the carding machine the fiber length and nep number are measured; the measured values must correspond to precisely defined criteria. If it is not feasible to maintain such values within the predetermined magnitudes by regulating the carding machine, an attempt is first made to improve such values by setting the fine cleaning machine anew. If again, such an attempt is unsuccessful, it is necessary to change the mixing ratio which has to be performed by an appropriate control of the bale opener; this also affects the bale stock.

In such a method the individual magnitudes, that is, the value of nep number and fiber length are measured and a new setting of the carding machine is effected based on the individual magnitudes of nep number and fiber length. By virtue of a certain card setting either the nep number may be reduced or, by means of a different card setting, the fiber length may be changed. Although a significant reduction in the nep number might be obtained by changing the setting magnitude of, for example, a card setting, a substantial negative change of the fiber length may simultaneously occur, or conversely. Conventional processes are based on the assumption that an improvement of both individual measuring magnitudes, namely the reduction of the nep number and the improvement in the staple (fiber length) may not be achieved merely by setting the carding machine, but rather, the mixing ratio of the fiber material must also be changed.

SUMMARY OF THE INVENTION

It is an object of the invention to provide an improved method and apparatus of the above-outlined type from which the discussed disadvantages are eliminated and which makes possible a substantial reduction in the nep number and a low level of damaging (fiber length shortening) in the carding machine.

This object and others to become apparent as the specification progresses, are accomplished by the invention, according to which, briefly stated, the method of measuring fiber material while being processed by fiber processing components of a carding machine, includes the following steps: measuring fiber length and nep number at an outlet of the carding machine; applying measured values of the fiber length and nep number to a control and regulating device; forming, in the control and regulating device, optimized machine setting data for the fiber length and the nep number; and applying the optimized machine setting data to at least one of the fiber processing components affecting fiber length and nep number.

By virtue of the fact that the measuring values for the nep number and the measuring values for the fiber length (fiber shortening) are coupled to one another, a significant reduction in the nep number and, at the same time, a low level of fiber damage (fiber shortening) may be achieved, contrary to the conventional method practiced heretofore. The measuring values for the nep number and the fiber length are combined and utilized for regulation. In this manner, an optimization is achieved in a particularly advantageous way.

The method according to the invention has the following additional advantageous features:

The fiber length distribution is measured on-line.

The processing component changes the carding intensity.

The rpm of the carding cylinder and/or the distance between the clothing of the carding cylinder and the clothings of the traveling flats or stationary flats are changed.

The nep number is measured in the fiber material at the inlet and/or at the outlet of the carding machine.

The fiber length is measured at the inlet and/or the outlet of the carding machine.

An optimal setting of the processing component of the carding machine is effected based on the dependence of the nep number from the setting of a processing element on the one hand and based on the dependence of the fiber length from the setting of the processing element, on the other hand.

The dependency of the fiber length from the setting of the processing element is utilized for more than one fiber type. The input data for the fiber length and the nep number are compared with inputted characteristic curves.

The invention also relates to an apparatus integrated in a carding machine for processing textile fibers, such as cotton, chemical fibers or the like in which at the outlet of the carding machine the fiber length and the nep number may be measured and a regulation of the carding machine is provided in which the measuring values for the fiber length and the measuring values for the nep number are utilized as input data and applied to a control and regulating apparatus. The control and regulating apparatus processes the inputted data concerning fiber length and nep number and compares the data with an earlier inputted (stored) characteristic curve to thus determine optimized machine setting data. Based on such data at least one fiber processing component of the carding machine is set for affecting the nep number and the fiber length.

The apparatus according to the invention has the following additional advantageous features:

The fiber length is measurable on-line.

A fiber shortening sensor is provided.

A fibrograph is provided for measuring the fiber length distribution.

The nep number is measured on-line.

A camera having an electronic image evaluating device is provided for measuring the nep number.

The setting member is an rpm-regulated motor for driving the carding cylinder.

The setting member is at least one setting motor such as a stepping motor for setting the distance between the clothing of the carding cylinder and the clothings of the traveling flats and/or stationary flats.

An electronic control and regulating device such as a microcomputer is provided to which there are connected at least one measuring device for the nep number and at least one setting member for a processing element which affects the nep number and the fiber length.

From the measuring values electric signals may be derived.

The setting member are actuators for setting the flexible bends or the like of the carding machine.

DESCRIPTION OF THE PREFERRED EMBODIMENTS

Figure 1:
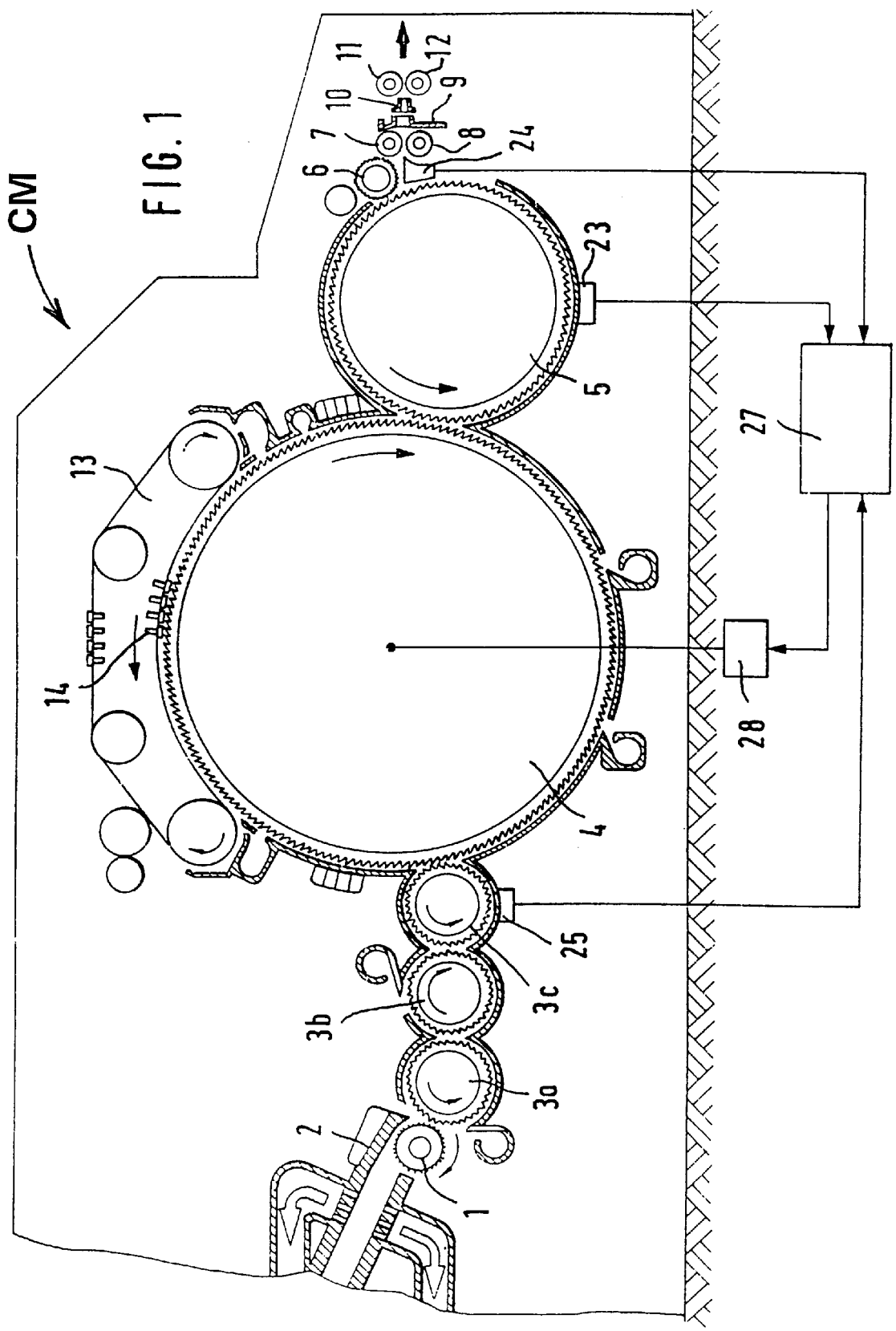
FIG. 1 is a schematic side elevational view of a carding machine incorporating the apparatus according to the invention.

FIG. 1 illustrates a carding machine CM which may be an EXACTACARD DK 803 model, manufactured by Trutzschler GmbH & Co. KG, Monchengladbach, Germany. The carding machine CM has a feed roller 1, a feed table 2 cooperating therewith, licker-ins 3a, 3b, 3c, a main carding cylinder 4, a doffer 5, a stripping roll 6, a pair of cooperating crushing rolls 7, 8, a web guiding element 9, a sliver trumpet 10, a pair of cooperating calender rolls 11, 12 and traveling flats 13 including flat bars 14.

Underneath the doffer 5 a measuring element 23 (sensor) is positioned for measuring the fiber lengths (staple) and underneath the stripping roll 6 a measuring element 24 is arranged for detecting the nep number of the fiber web. Underneath the licker-in 3c a measuring element 25 is situated for detecting fiber lengths. The measuring elements 23, 24 and 25 are connected with an electronic control and regulating device 27, such as a microcomputer, an output of which is coupled to an rpm-regulated motor 28 for driving the main carding cylinder 4. The direction of rotation of the various rolls and rollers is indicated by respective curved arrows.

Figure 2:
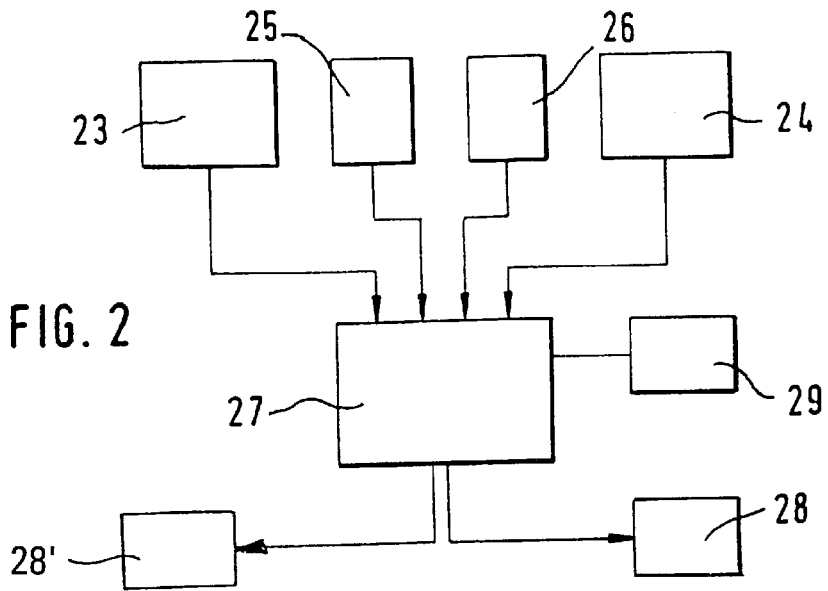
FIG. 2 is a block diagram of an electronic control and regulating device to which at least a nep sensor, a fiber length sensor and a control device, such as a motor are connected.

As shown in FIG. 2, to the control and regulating device 27 there are connected the measuring member 23, the measuring member 24, the measuring member 25 for detecting the fiber lengths at the input of the carding machine, for example, at the licker-in 3c, a measuring member 26 for detecting the nep number at the input of the carding machine, a desired value setting device 29, the drive motor 28 of the carding cylinder 4 and a motor 28' which varies the distance between the clothings of the flat bars 14 and the clothing of the main carding cylinder 4 (see FIG. 6) and thus alters the carding intensity.

Figure 6:
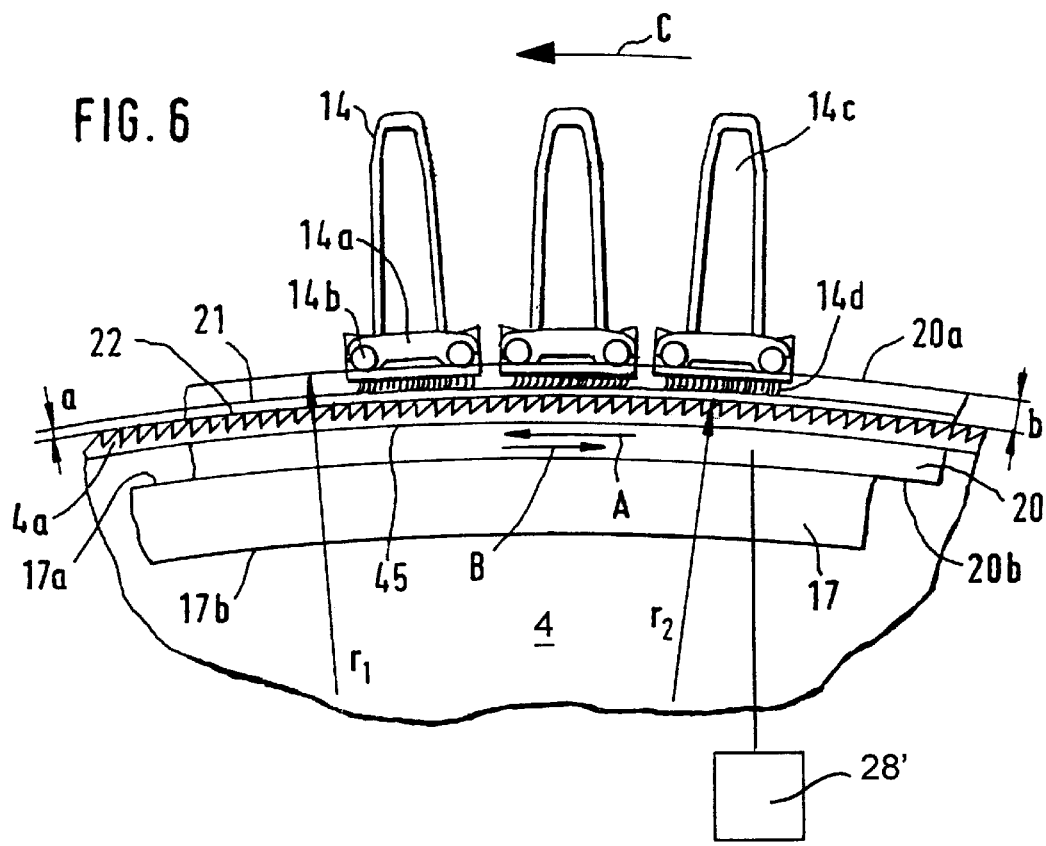
FIG. 6 is a schematic fragmentary side elevational view of a carding cylinder cooperating with flat bars and also showing flexible bends.

The measuring member 24 for automatically detecting the nep number is connected to the electronic control and regulating device (microcomputer) 27 and may be, for example, a NEPCONTROL NCT model, manufactured by Trüatzschler GmbH & Co. KG. The measuring values for a fiber length which, for example, are determined by a fibrograph, may also be inputted in the electronic control and regulating device 27 by means of an inputting device. Also, a switching element, for example, a push button or the like may be connected to the electronic control and regulating device 27 to activate the drive motor 28. Further, a measuring member, for example, a FLATCONTROL FCT model, manufactured by Trutzschler GmbH & Co. KG may be connected to the electronic control and regulating device 27 for detecting the distance a between the points 21 of the flat bar clothings 13d and the points 22 of the cylinder clothing 4a (FIG. 6).

Figure 3:
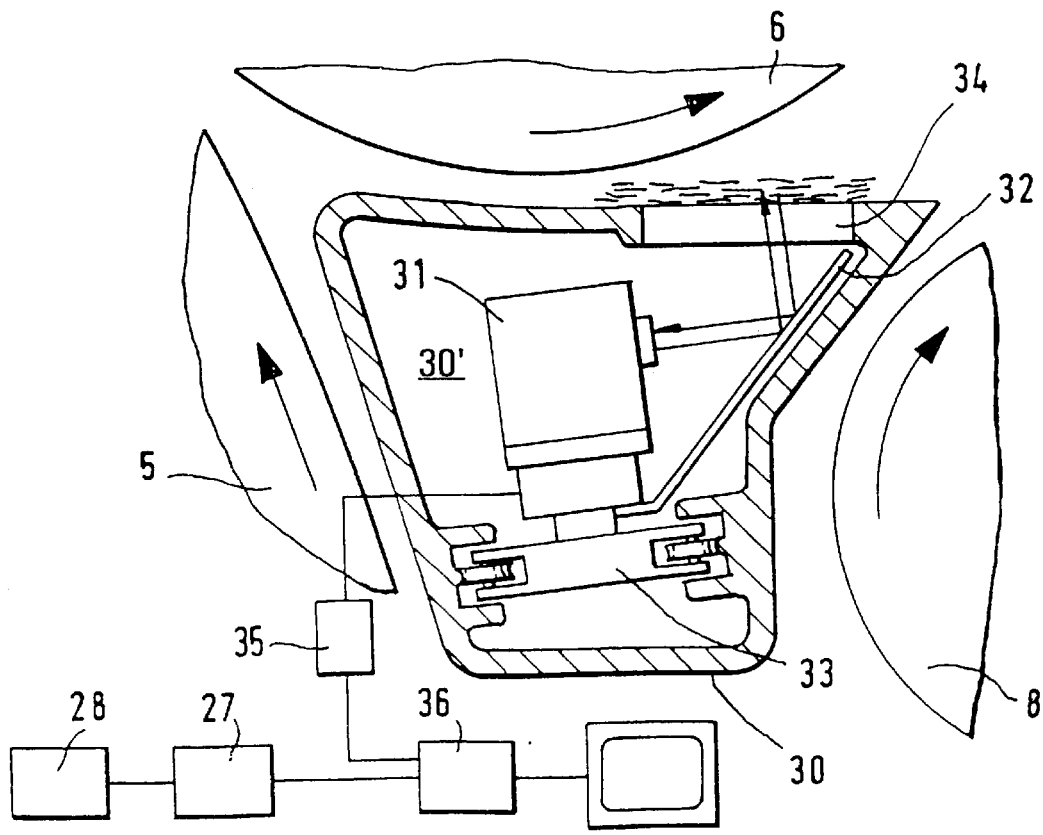
FIG. 3 is a schematic, partially sectional side elevational view of a device positioned underneath the stripping roll of the carding machine for recognizing impurities, such as neps, by means of a camera as well as a block diagram illustrating the connection of the camera to an electronic control and regulating device.

Turning to FIG. 3, underneath the stripper roll 6 a supporting and guiding element 30 is provided, having a cavity 30'. A carriage 33, a camera 31, a non-illustrated illuminating device and a mirror 32, all mounted on the carriage 30 are arranged in the cavity 30'. The supporting and guiding element 30 is provided with a window 34 on which the fiber web runs and whose nep number is detected by the camera 31. The camera 31 is connected with an image processing device 36 via a computer 35. The device 36, in turn, is connected to the control and regulating device 27, an output of which is connected to the motor 28 to thus regulate the speed (and, as a result, the carding intensity) of the carding cylinder 4. As an alternative or as a complementation, a setting member constituted by the motor 28' may be connected to control and regulating device 27 for changing the nep number and the fiber shortening by changing the distance a between the clothings of the flat bars 14 and the clothing of the main carding cylinder 4. It is likewise feasible to regulate in a similar manner the distance of a mote knife from a roll (for example, one or more of the licker-ins 3a, 3b, 3c), or the position of a guide element, or the like.

Figure 4:
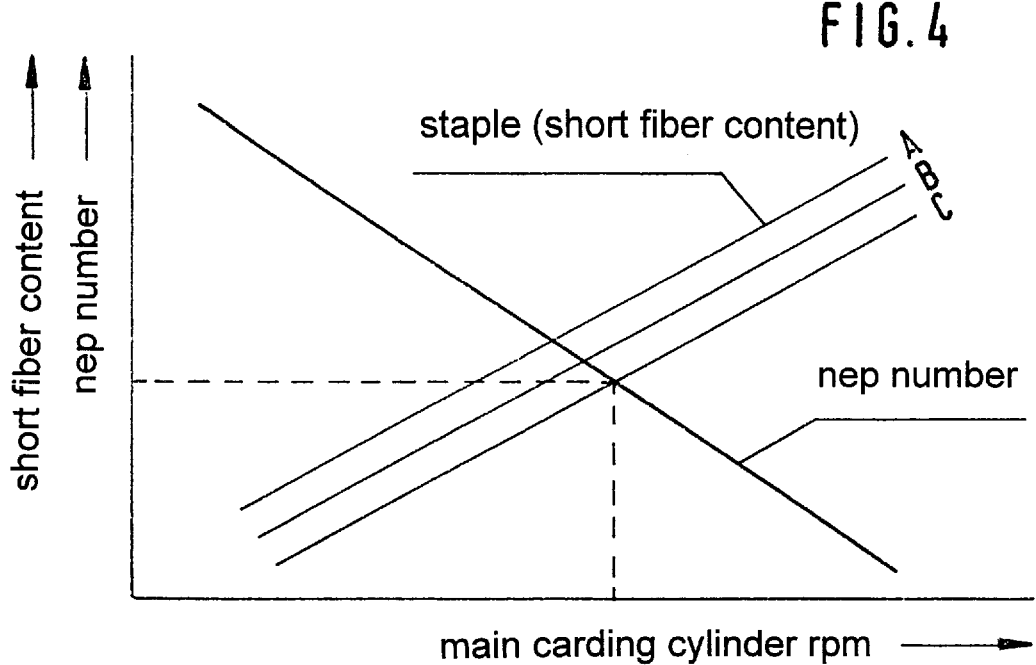
FIG. 4 is a diagram illustrating the short fiber content and nep number as a function of the main carding cylinder rpm for various fiber types.

As shown in the diagram of FIG. 4, as the rpm of the carding cylinder 4 increases, the nep number decreases and the fiber shortening effect increases. The curve for the fiber shortening is shown for fiber types (qualities) A, B and C. The point of intersection between the curves for the nep number and for the fiber shortening determines the optimum nep number and the cylinder rpm associated therewith, as illustrated in broken lines for the fiber type C. Such an optimum is computed and determined in the control and regulating device 27 from the inputted curves of the nep number and the fiber shortening. In this process, a comparison is effected with characteristic curves which are present in the desired value memory 29.

Figure 5:
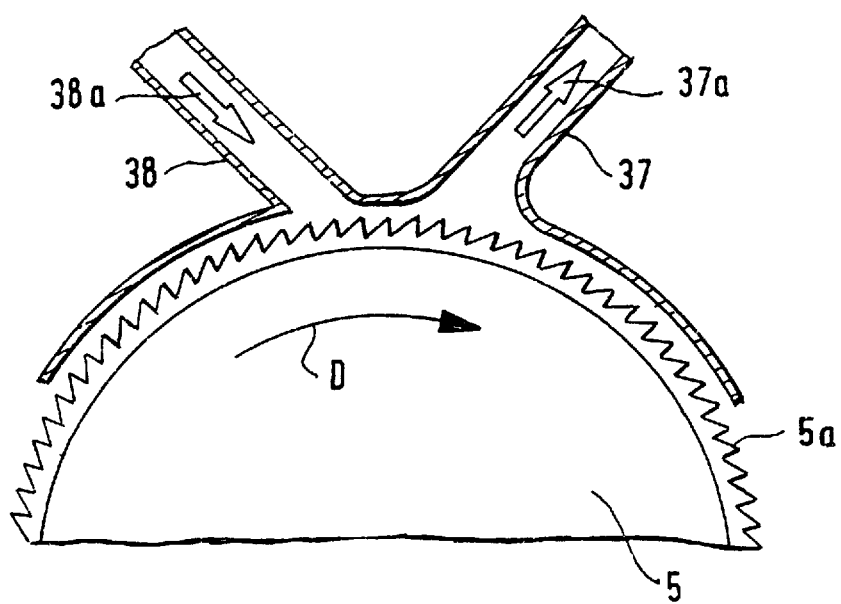
FIG. 5 is a schematic side elevational view of a device for removing small fiber samples from a clothed roll by means of the combined action of a vacuum stream and a compressed air stream.

In FIG. 5, above the doffer 5 a conduit 37 communicates with the space through which fiber material is advanced by the doffer 5. The conduit 37 which is oriented obliquely to the clothing of the doffer 5 is coupled to a non-illustrated vacuum source (such as the intake side of a blower), by means of which a suction stream 37a is generated periodically and at random for entraining small quantities (samples) of fiber from the clothing of the doffer 5. These fibers are subsequently analyzed for determining the fiber length distribution. The fiber quantities drawn away from the doffer 5 are so small that the uniformity of the sliver produced is practically not affected. Based on the sample analysis, a staple diagram or data therefor are generated. Upstream and in the vicinity of the suction conduit 37, as viewed in the rotary direction D, a conduit 38 communicates with the space through which fiber material is advanced by the doffer 5. The conduit 38 is coupled to a non-illustrated air pressure source (such as the output side of a blower), by means of which a compressed air stream 38a is generated which supports the suction effect of the vacuum stream 37a.

Turning to FIG. 6, on each side of the carding machine flexible bends 17 (only one is visible), including a plurality of setting screws, are attached to the frame of the carding machine such that the flexible bends 17 flank an upper peripheral portion of the main carding cylinder 4. Each flexible bend 17 has a convex outer surface 17a and an underside 17b. Above the flexible band 17 a sliding guide 20 is arranged which is made of a low-friction plastic material and which has a convex outer surface 20a and a concave inner surface 20b. The concave inner surface 20b of the sliding guide 20 lies on the convex outer surface 17a of the flexible bend 17 and may slide thereon in the direction of arrows A and B. The flat bars 14 have, at opposite ends, a bar head 14a from which project two axially oriented steel pins 14b which slide on the convex outer face 20a of the sliding guide 20 in the direction of the arrow C. The flat bar clothing 14d is mounted on the underface of the carrier body 14c of the flat bar 14. An imaginary circle contacting the point series of the flat bar clothings 14d is designated at 21. The carding cylinder 4 has on its circumference a cylinder clothing 4a which may be, for example, a sawtooth clothing. An imaginary circle contacting the point series of the cylinder clothings 4a is designated at 22. The distance between the concentric circles 21 and 22 is designated at a and is, for example, 0.20 mm. The distance between the convex outer face 20a and the circle 22 is designated with b. The radius of the convex outer face 20a is designated at $r_1$ whereas the radius of the circle 22 is designated at $r_2$. The radii $r_1$ and $r_2$ intersect in the rotary axis of the main carding cylinder 4. The sliding guide 20 may be shifted in the radial direction $r_1$ by means of a setting member such as the motor 28' to vary the distance a and to thus change the carding intensity.

Figure 7:
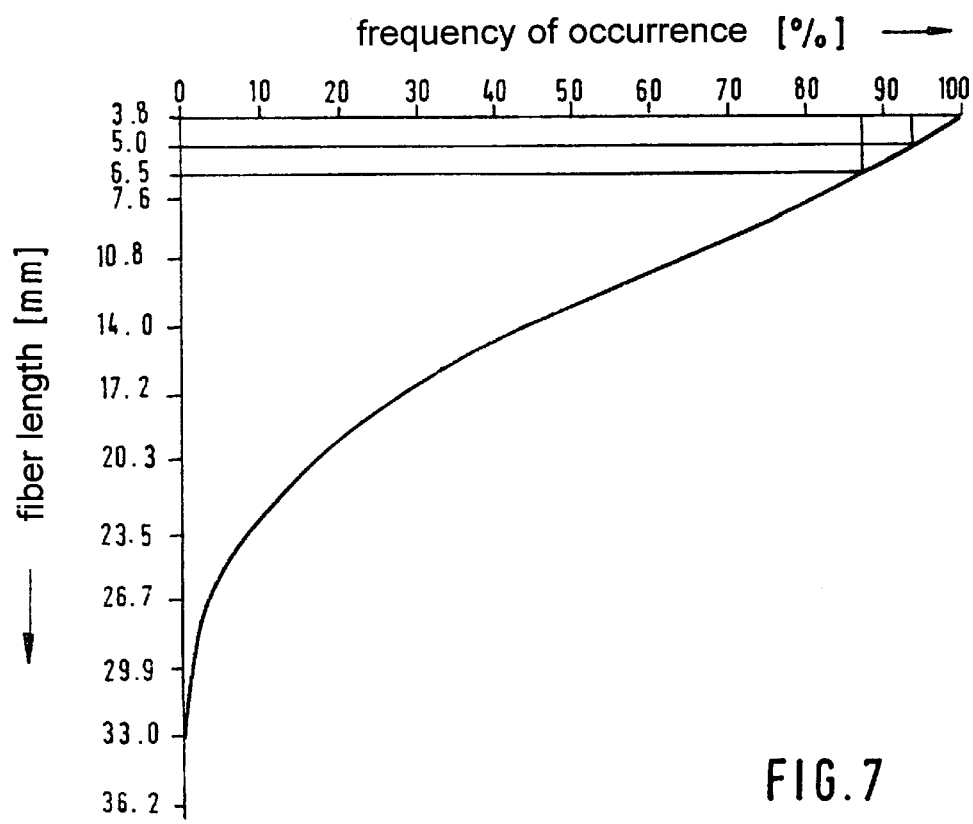
FIG. 7 is a diagram illustrating an occurrence frequency for determining data which are inputted in the control and regulating device for setting the carding intensity.

A sample is removed from the fiber material entrained by the doffer 5 and subjected to an analysis which is to serve subsequently for setting the carding intensity of the carding machine. Such an analysis is performed, for example, with the aid of a fibrograph which generates a fibrogram illustrating the length distribution of the fibers. Such a length distribution is illustrated in the diagram of FIG. 7. The horizontal axis represents the frequency in percentage while the vertical axis indicates the fiber length in mm. The exemplary fibrogram illustrated in FIG. 7 shows that 100% of all fibers have a length of at least 3.8 mm. Approximately 93% of all fibers have a length of more than 5 mm and approximately 88% of all fibers have a length of over 6.5 mm. As further shown by the diagram, the greater the fiber length, the smaller the proportion of the fibers to the entire fiber quantity until eventually, at a fiber length of approximately 35 mm, no more fiber may be found. It was found that fibers shorter than 5 to 6.5 mm do not contribute to the strength of the spun yarn. For this purpose, based on the curve shown in FIG. 7, it is determined how much percentage of all fibers have a length which is less than the set smallest length of 5 to 6.5 mm. The fibrogram shows for 5 mm, for example, that 5% of all fibers are shorter than 5 mm. The curve further shows that 12% of all fibers are shorter than 6.5 mm. The thus-determined 7 to 12% serve, as already indicated above, for setting the carding intensity of the carding machine. The data for the staple diagram are electronically inputted into the control and regulating device 27 which from these data and from data representing the nep number computes an optimum value which serves for setting the carding intensity of the carding machine.

Further, by means of the apparatus and the method according to the invention, for a given carding cylinder rpm a value pair for the short fiber proportion and the nep number may be determined based on the diagram of FIG. 4, externally of the point of intersection of the two curves.

It will be understood that the above description of the present invention is susceptible to various modifications, changes and adaptations, and the same are intended to be comprehended within the meaning and range of equivalents of the appended claims.

What is claimed is:

1. A method of measuring fiber material while being processed by fiber processing components of a carding machine, comprising the following steps:

(a) measuring fiber length and nep number at an outlet of the carding machine;

(b) applying measured values of the fiber length and nep number to a control and regulating device;

(c) forming, in said control and regulating device, optimized machine setting data for the fiber length and the nep number; and (d) applying said optimized machine setting data to at least one of said fiber processing components affecting fiber length and nep number.

2. The method as defined in claim 1, further comprising the step of removing a partial fiber quantity from the fiber material at one of said fiber processing components; wherein said step of measuring fiber length is performed on the removed partial fiber quantity.

3. The method as defined in claim 2, wherein said step of removing includes the step of generating a suction stream for entraining said partial fiber quantity.

4. The method as defined in claim 3, further comprising the step of generating a stream of compressed air directed into said suction stream for aiding a suction effect thereof.

5. The method as defined in claim 1, wherein said carding machine includes a doffer; and further wherein said step of measuring fiber length is performed at said doffer.

6. The method as defined in claim 1, wherein said carding machine includes a stripper roll; and further wherein said step of measuring fiber length is performed at said stripper roll.

7. The method as defined in claim 1, wherein said carding machine includes a pair of cooperating crushing rolls; and further wherein said step of measuring fiber length is performed in a vicinity of said crushing rolls.

8. The method as defined in claim 1, wherein said carding machine includes a licker-in; further comprising the step of measuring fiber length at said licker-in.

9. The method as defined in claim 1, wherein the carding machine includes a carding cylinder and flats cooperating with the carding cylinder; wherein said carding cylinder and said flats carry clothings; said clothings forming two of said fiber processing components; and further wherein step (d) comprises the step of varying the distance between the clothing of the carding cylinder and the clothing of the flats for varying the carding intensity to which the fiber material is exposed.

10. The method as defined in claim 1, wherein said carding machine has an inlet and an outlet; further comprising the step of measuring nep number at said inlet.

11. The method as defined in claim 1, wherein said fiber processing components are clothings; and further wherein step (d) comprises the step of applying the optimized data to at least one of said clothings.

12. A carding machine having
(a) a fiber inlet zone;
(b) a fiber outlet zone;
(c) fiber processing components disposed in said inlet and outlet zones and therebetween for consecutively treating fiber as the fiber passes through the carding machine from the inlet zone to the outlet zone;
(d) measuring means for measuring fiber length and nep number in a fiber mass during passage thereof through said outlet zone;
(e) an electronic control and regulating device connected to said measuring means for receiving measuring data from said measuring means related to the fiber length and the nep number; said electronic control and regulating device including means for comparing said measuring data with characteristic curves stored in said electronic control and regulating device to obtain optimized machine setting data; and
(f) means for applying said optimized machine setting data to at least one of said fiber processing components affecting fiber length and nep number.

13. The carding machine as defined in claim 12, further comprising a fibrograph for measuring a fiber length distribution.

14. The carding machine as defined in claim 12, wherein said measuring means for measuring nep number includes a camera having an electronic image evaluating device.

15. The carding machine as defined in claim 12, wherein said fiber processing components include a carding cylinder and flats cooperating with the carding cylinder; wherein said carding cylinder and said flats carry clothings; wherein said means for applying said optimized machine setting data is a setting member for varying a distance between the clothing of said carding cylinder and the clothings of said flats.

16. The carding machine as defined in claim 12, wherein said measuring means comprises a measuring device for measuring fiber length and a measuring device for measuring nep number; wherein said means for applying said optimized machine setting data is a setting member connected to said one fiber processing component.

17. The carding machine as defined in claim 12, further comprising a carding cylinder having an rpm-regulated drive motor; further wherein said means for applying said optimized machine setting data is formed by said rpm-regulated drive motor.

* * * * *